US007348034B2

(12) United States Patent
Murray et al.

(10) Patent No.: US 7,348,034 B2
(45) Date of Patent: Mar. 25, 2008

(54) PLANT BASED FORMULATIONS FOR IMPROVING SKIN MOISTURE, TEXTURE, AND APPEARANCE

(75) Inventors: Mary A. Murray, Irvine, CA (US); Aaron W. Crawford, Los Angeles, CA (US); David J. Fast, Grand Rapids, MI (US); Dora Dong, Guangzhou (CN); Michael Huang, Guangzhou (CN); Lynne Marie Connor, Grand Rapids, MI (US)

(73) Assignee: Access Business Group International LLC, Ada, MI (US)

(*) Notice: Subject to any disclaimer, the term of this patent is extended or adjusted under 35 U.S.C. 154(b) by 70 days.

(21) Appl. No.: 11/075,006

(22) Filed: Mar. 7, 2005

(65) Prior Publication Data
US 2006/0198810 A1 Sep. 7, 2006

(51) Int. Cl.
A61K 36/73 (2006.01)
A61K 36/87 (2006.01)
A61K 36/815 (2006.01)
(52) U.S. Cl. ...................... 424/765; 424/766
(58) Field of Classification Search ............ None
See application file for complete search history.

(56) References Cited

U.S. PATENT DOCUMENTS

| | | | |
|---|---|---|---|
| 5,290,605 A | 3/1994 | Shapira | |
| 5,466,452 A | 11/1995 | Whittle | |
| 5,520,991 A | 5/1996 | Eustatiu | |
| 5,925,348 A * | 7/1999 | Riley et al. | 424/94.5 |
| 5,976,568 A | 11/1999 | Riley | |
| 5,997,852 A | 12/1999 | Yoneda et al. | |
| 6,149,939 A | 11/2000 | Strumor et al. | |
| 6,254,898 B1 | 7/2001 | Bragaglia | |
| 6,280,751 B1 | 8/2001 | Fletcher et al. | |
| 6,375,992 B1 | 4/2002 | Blumenstein-Stahl et al. | |
| 6,602,529 B1 * | 8/2003 | Lonergan et al. | 426/128 |
| 6,605,296 B1 | 8/2003 | Stuckler | |
| 6,682,763 B2 | 1/2004 | Kuno et al. | |
| 2002/0127256 A1 | 9/2002 | Murad | |
| 2004/0013749 A1* | 1/2004 | Young et al. | 424/732 |
| 2004/0081628 A1 | 4/2004 | Gierhart et al. | |
| 2004/0162292 A1 | 8/2004 | Evenstad et al. | |

FOREIGN PATENT DOCUMENTS

ZA 9605149 A * 3/1997

OTHER PUBLICATIONS

Koya-Miyata S et al. Identification of a collagen production-promoting factor from an extract of royal jelly and its possible mechanism. Biosci Biotechnol Biochem. Apr. 2004;68(4):767-73.
Shi J et al. Polyphenolics in grape seeds-biochemistry and functionality. J Med Food. 2003 Winter;6(4):291-9.
Yamakoshi J et al. Lightening effect on ultraviolet-induced pigmentation of guinea pig skin by oral administration of a proanthocyanidin-rich extract from grape seeds. Pigment Cell Res. 2003;16:629-38.
Taniguchi Y et al. Oral administration of royal jelly inhibits the development of atopic dermatitis-like skin lesions in NC/Nga mice. Int Immunopharmacol. Sep. 2003;3(9):1313-24.
Deng HB et al. Inhibiting effects of *Achyranthes bidentata* polysaccharide and *Lycium barbarum* polysaccharide on nonenzyme glycation in D-galactose induced mouse aging model. Biomed Environ Sci. Sep. 2003;16(3): 267-75.
Gonzalez S et al. Dietary lutein/zeaxanthin decreases ultraviolet B-induced epidermal hyperproliferation and acute inflammation in hairless mice. J Invest Dermatol. Aug. 2003;121(2):399-405.
Sies H et al. Non-nutritive bioactive constituents of plants: lycopene, lutein and zeaxanthin. Int J Vitam Nutr Res. Mar. 2003;73(2):95-100.
Deng Y et al. Effect of *Angelica sinensis* (Oliv.) on melanocytic proliferation, melanin synthesis and tyrosinase activity in vitro. Di Yi Jun Yi Da Xue Xue Bao. Mar. 2003;23(3):239-41 (See Abstract; first page).
Heinrich U et al. Supplementation with β-carotene or a similar amount of mixed carotenoids protects humans from UV-induced erythema. Am Soc Nutri Sciences 2003:98-101.
Morganti P et al. Role of topical and nutritional supplement to modify the oxidative stress. Int J Cosmetic Science. 2002; 24:331-339.
Huh CH et al. A randomized, double-blind, placebo-controlled trial of vitamin C iontophoresis in melasma. Dermatology 2003; 206:316-320.
McArdle F et al. UVR-induced oxidative stress in human skin in vivo: effects of oral vitamin C supplementation. Free Radic Biol Med 2002; 33:1355-1362.
Burke KE et al. Effects of topical L-selenomethionine with topical and oral vitamin E on pigmentation and skin cancer induced by UV irradiation in Skh:2 hairless mice. J Am Acad Dermatol 2003; 49:458-72.
Yamamura T et al. Antimelanogenic activity of hydrocoumarins in cultured normal human melanocytes by stimulating intracellular glutathione synthesis. Arch Dermatol Res 2002; 294:349-54.
Hayakawa R et al. Effects of combination treatment with vitamins E and C on chloasma and pigmented contact dermatitis. A double blind controlled clinical trial. Acta Vitaminol Enzymol 1981; 3:31-8.

(Continued)

*Primary Examiner*—Susan Coe Hoffman
(74) *Attorney, Agent, or Firm*—Brinks Hofer Gilson & Lione

(57) ABSTRACT

The present invention relates to formulations of ingredients that are useful for improving the appearance, texture and/or moisture of skin. In particular, the formulations of the present invention stimulate collagen, elastin, and lipid synthesis and/or inhibit or minimize the loss of collagen, elastin, and lipids in the skin. Additionally, the formulations of the present invention inhibit matrix metalloproteases, such as MMP-1, MMP-9, collagenase, or elastase.

19 Claims, 6 Drawing Sheets

OTHER PUBLICATIONS

Misir R et al. Effect of biotin supplementation of a barley-wheat diet on restoration of healthy feet, legs and skin of biotin deficient sows. Research in Veterinary Science. 1986; 40:212-218.

Frigg M et al. Clinical study on the effect of biotin on skin conditions in dogs. Schweiz Arch Tierheilkd. 1989; 131:621-625.

Khanna S et al. Upregulation of oxidant-induced VEGF expression in cultured keratinocytes by a grape seed proanthocyanidin extract. Free Radic Biol Med 2001: 31(1):38-42.

Khanna S et al. Dermal wound healing properties of redox-active grape seen proanthocyanidins. Free Radic Biol Med 2002; 33(8):1089-1096.

Zhao J et al. Anti-tumor-promoting activity of a polyphenolic fraction isolated from grape seeds in the mouse skin two-stage initiation-promotion protocol and identification of procyanidin B5-3'-gallate as the most effective antioxidant constituent. Carcinogenesis. 1999; 20(9):1737-1745.

Altavilla D et al. Inhibition of lipid peroxidation restores impaired VEGF expression and stimulates wound healing and angiogenesis in the genetically diabetic mouse. Diabetes. Mar. 2001;50:667-674.

Kartnig T. Clinical applications of *Centella asiatica* (L) Urb: in Craker LE et al, eds. Herbs, spices, and medicinal plants: Recent advances in botany, horticulture, and pharmacology, New York, NY: The Oryx Press, 1988; 3:145-173.

Masquelier J et al. Stabilisation du collagene par les oligomeres procyanidoliques. Acta Therapeutica 1981; 7(2):101-5 (See Summary, last page).

Jonadet M et al. Anthocyanosides extracted from *Vitis vinifera, Vaccinium myrtillus* and *Pinus maritimus*. I. Elastase-inhibiting activities in vitro. II. Comparative angioprotective activities in vivo. Journal of Pharmacology (Belgium) 1983; 38:41-46 (See Summary, first page).

Robert L et al. Action des oligomeres procyanidoliques sur la permeabilite de la paroi vasculaire. Etude par morphologie quantitative. Pathologie Biologie 1990: 38(6):608-616.

Ni Z et al. Treatment of melasma with pycnogenol. Phytother Res 2002; 16:567-571.

Swatschek D et al. Marine sponge collagen: isolation, characterization and effects on the skin parameters surface-pH, moisture and sebum. Eur J Pharm Biopharm 2002: 53:107-113.

Fujita T et al. The effect of active absorbable algal calcium (AAA Ca) with collagen and other matrix componenets on back and joint pain and skin impedance. J Bone Miner Metab 2002; 20:298-302.

Greco RM et al. Hyaluronic acid stimulates human fibroblast proliferation within a collagen matrix. J Cell Physiol 1998; 177:465-473.

Kim SJ et al. The effect of glycolic acid on cultured human skin fibroblasts: cell proliferative effect and increased collagen synthesis. J Dermatol 1998; 25:85-89.

Trabucchi E et al. Low molecular weight hyaluronic acid prevents oxygen free radical damage to granulation tissue during wound healing. Int J Tissue React 2002; 24:65-71.

Croce MA et al. Hyaluronan affects protein and collagen synthesis by in vitro human skin fibroblasts. Tissue & Cell 2001; 33(4):326-331.

br Purba, M et al. Skin wrinkling: Can food make a difference? J Am College Nutr 2001; 20(1):71-80.

\* cited by examiner

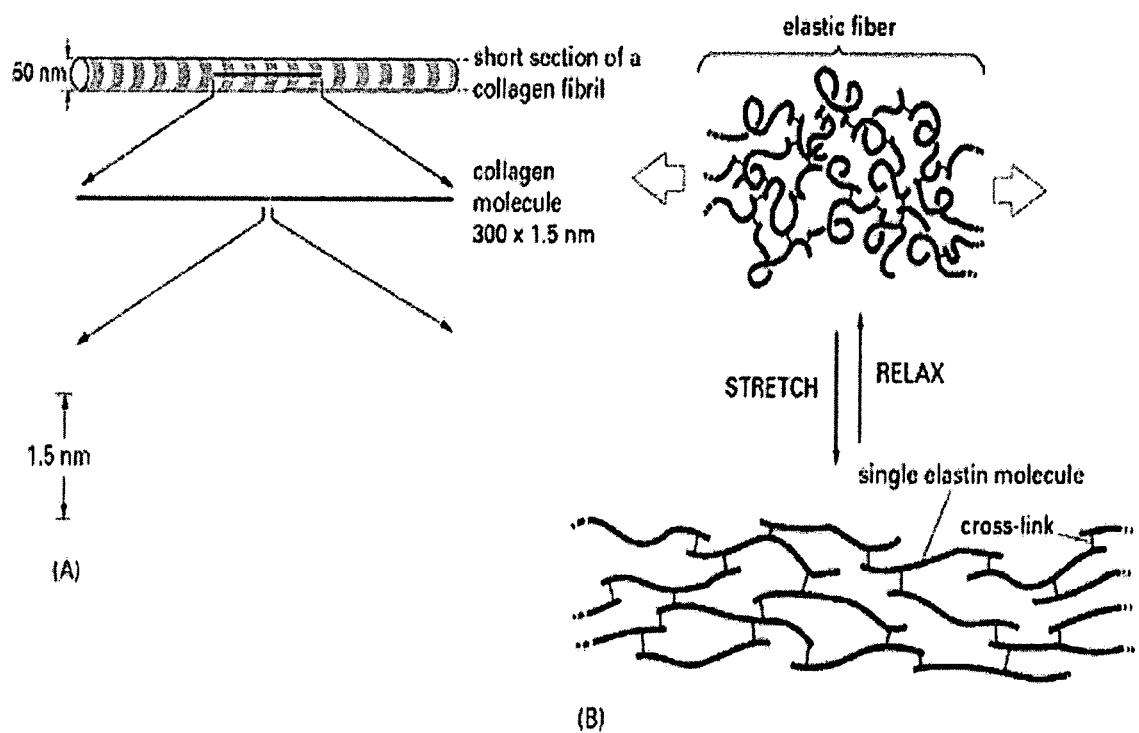
Figure 1. Structures of Collagen Fibrils and Elastin Fibers:

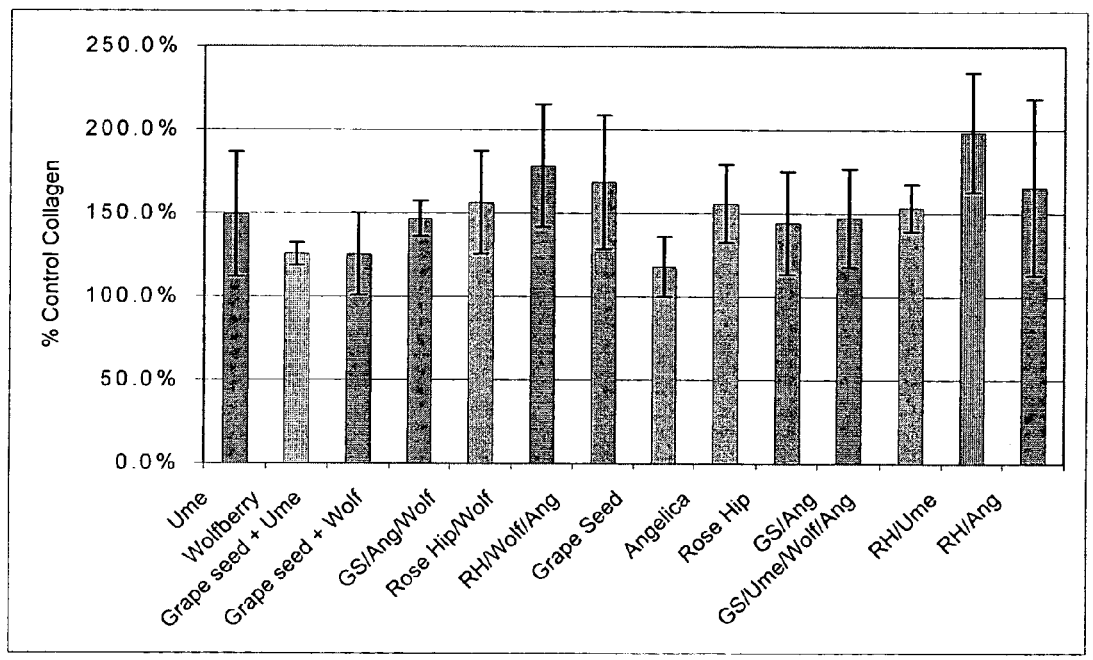
Figure 2. Effect of various ingredients, in combination or alone, on collagen synthesis:

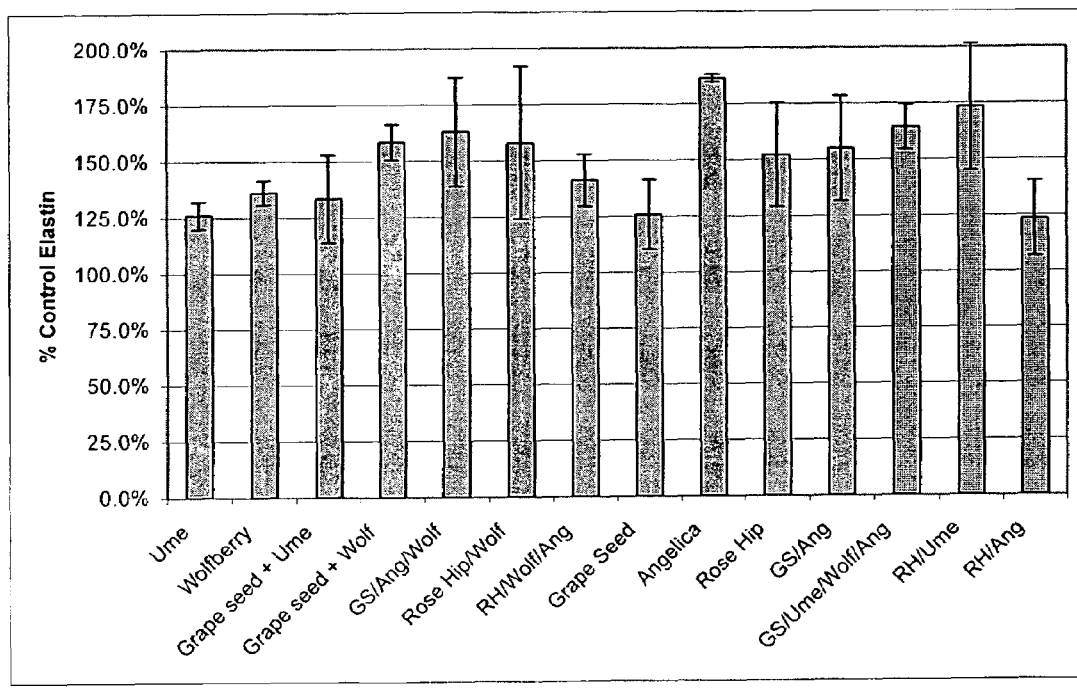
Figure 3. Effect of various ingredients, in combination or alone, on elastin synthesis:

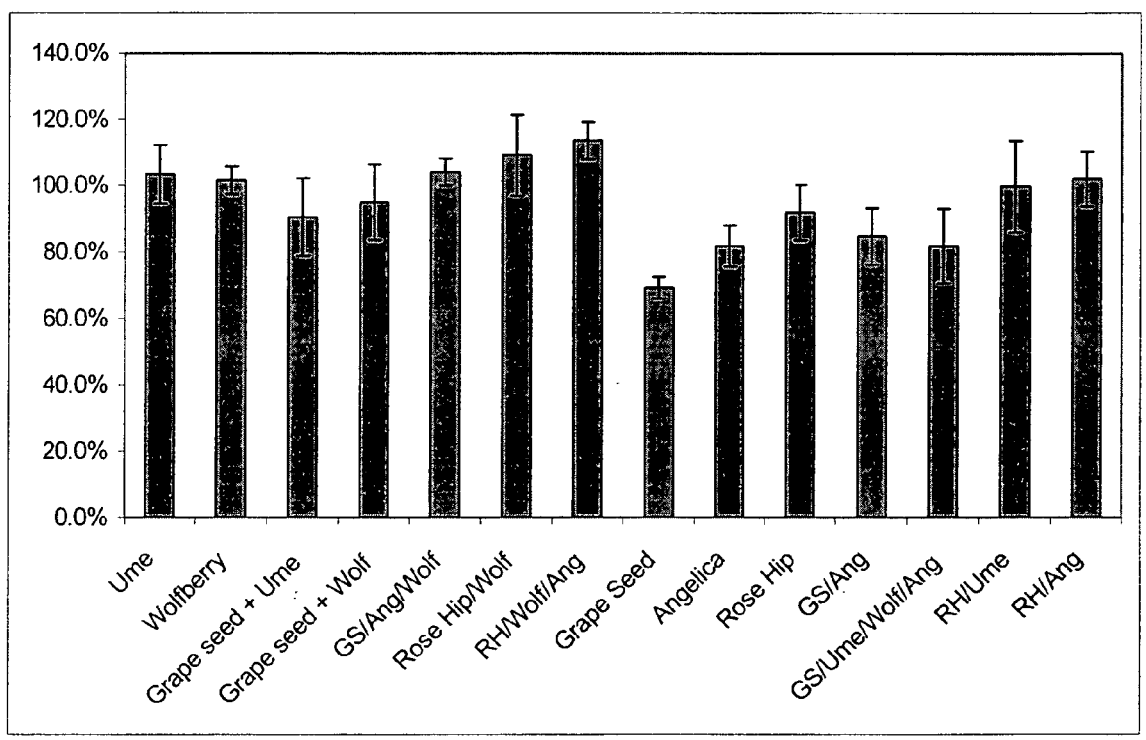
Figure 4. Effect of various ingredients, in combination or alone, on hyaluronic acid synthesis:

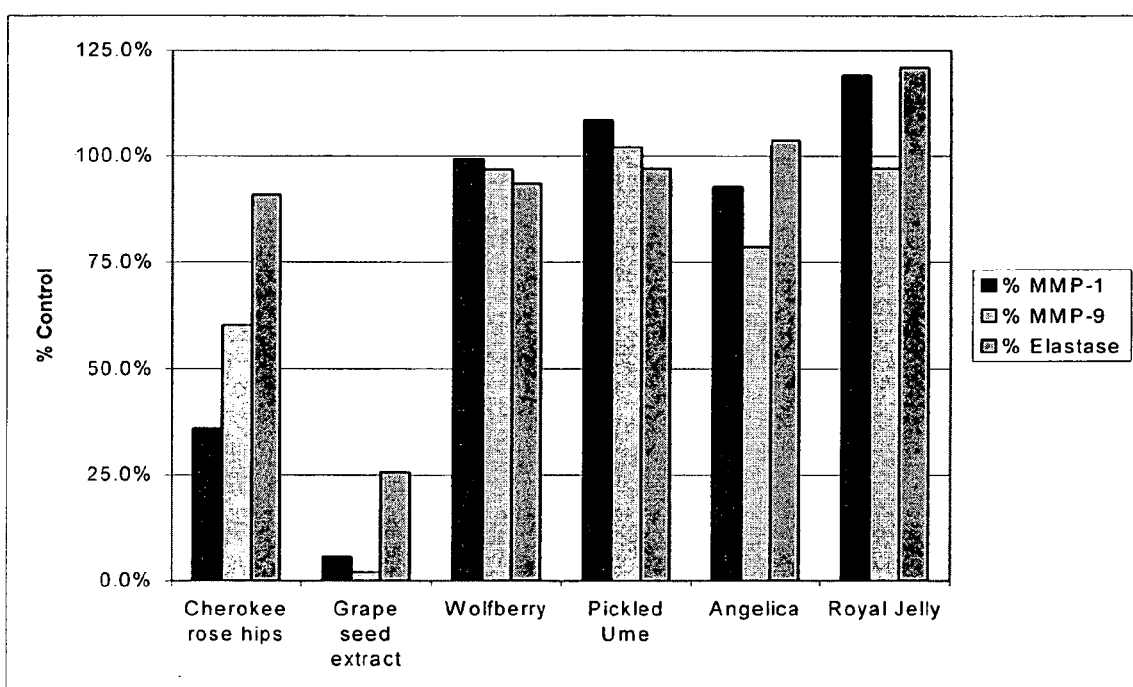
Figure 5. Enzyme Inhibition by Various Ingredients:

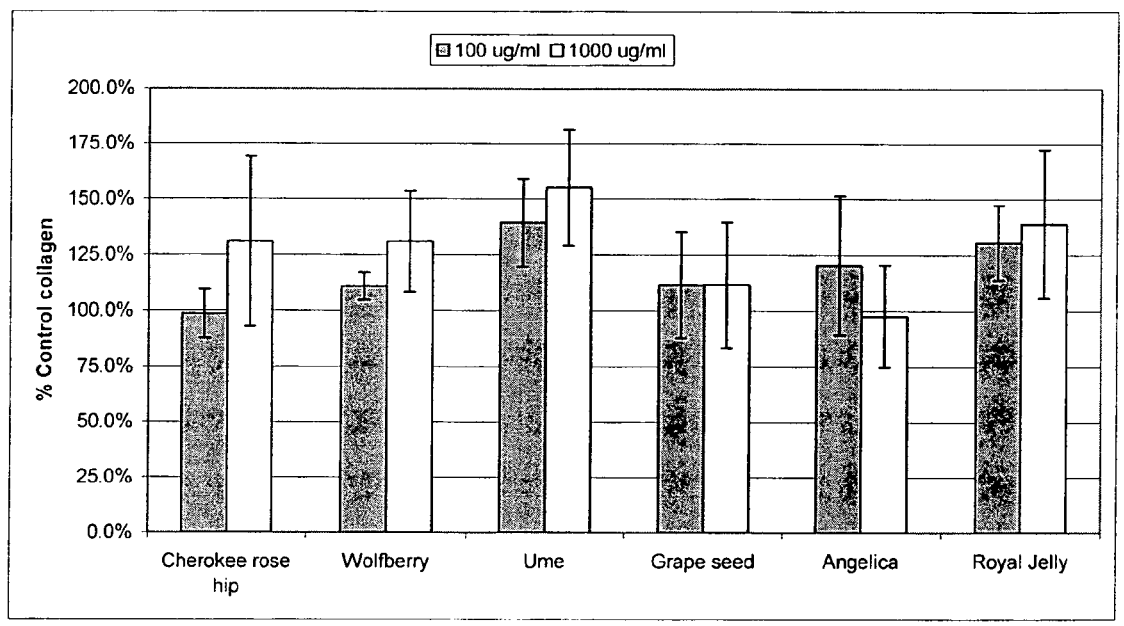
Figure 6. Transport of various ingredients across Caco-2 monolayers:

PLANT BASED FORMULATIONS FOR IMPROVING SKIN MOISTURE, TEXTURE, AND APPEARANCE

BACKGROUND

Evidence suggests the various signs and consequences of skin aging may be connected to cumulative oxidative damage incurred throughout one's lifetime. Poor diet, lack of exercise, and exposure to ultra violet light all cause oxidative damage. For example, ultra violet light is known to generate reactive oxygen species (ROS), such as superoxide, singlet oxygen, hydroxyl radicals, and hydrogen peroxide, in the skin. These ROS are known to degrade collagen in the skin and to decrease the ability of fibroblasts to produce collagen.

Collagen is the primary protein of connective tissue, which includes cartilage, bone, tendon, teeth, and skin. Collagen (in a pre-processed form called pro-collagen) is assembled in cells and consists of three polypeptides wound around each other in a triple helix form, which is stabilized by intrachain disulfide bonds. After the helical molecule is assembled and modified in the cell it is secreted into the extracellular medium and further processed to a mature form (tropocollagen).

Matured collagen molecules assemble into fibrils in the extracellular space in a staggered, parallel, fashion wherein the molecules are stabilized in this fibril pattern by covalent cross-linking bonds between the N-terminus of one molecule and the C-terminus of another. The collagen fibrils are interlaced and branched in skin.

Indeed, these interlaced, branched collagen fibrils provide the skin with its shape and firmness, while another skin protein, elastin, provides skin with its elasticity. Elastin coils and recoils like a spring and accounts for the elasticity of structures such the skin, blood vessels, heart, lungs, intestines, tendons, and ligaments. Elastin is normally not produced by the human body after puberty and aging begin.

Like all other proteins in the human body, collagen and elastin are constantly being degraded. Enzymes that degrade collagen and elastin are known as matrix metalloproteases (MMPs). These enzymes can be stimulated by ROS. Some known MMPs include collagenase, elastase, MMP-1, and MMP-9. Collagenase is an enzyme produced by fibroblast like synoviocytes that degrades collagen. Elastase degrades elastin. MMP-1 cleaves fibrillar collagens, such as types I, II, and III, resulting in denatured collagens (gelatins) that are further degraded by MMP-9, which degrades laminin and type IV collagen, components of the basement membrane. Thus, these MMP enzymes are involved in the reduction of collagen and elastin in the skin, which leads to the appearance of fine lines, wrinkles, age spots, and sagging skin.

Like loss of collagen and elastin due to oxidative damage from ROS and MMPs, loss of moisture contributes to skin aging. Indeed, the skin's capacity to retain water decreases with age, making the skin more vulnerable to dehydration and wrinkling. Lipids and fats in the skin help combat water loss by providing an epidermal barrier. This barrier also hinders the growth of bacteria, which can cause skin irritation and sensitivity, both of which contribute to aging of skin.

Therefore, a formulation containing oxidizable or antioxidant nutrients to combat ROS, oxidative damage, and loss of collagen and elastin, as well as agents that hydrate the skin or increase the synthesis of lipids in the skin, would be useful for improving the appearance, texture, and moisture of the skin and maintaining general skin health.

BRIEF SUMMARY

Skin aging is directly related to many causes including oxidative stress of the skin, loss of moisture from the skin, and degradation of important proteins in skin such as collagen and elastin. The present invention is a formulation comprising a unique combination of ingredients including amino acids, carbohydrates, plant extracts, and vitamins, and a method of using these ingredients to improve the moisture, texture, and appearance of the skin. The unique formulations of the present invention work by increasing the synthesis of skin proteins, such as collagen or elastin, and/or by preventing or slowing the degradation of such proteins. Additionally, the formulations of the present invention have the unique ability to increase the synthesis and/or prevent or slow the degradation of lipids in the skin, which aids in skin moisture. The formulations of the present invention can be topically administered, orally administered, administered by injection, peritoneally administered, or any combination thereof.

Accordingly, in one embodiment, the present invention provides a formulation comprising pollen (Royal Jelly), wolfberry extract, Chinese Angelica extract, grape seed extract, carotenoids, rose hips, Vitamin C or derivatives thereof, biotin, Vitamin E or derivatives thereof, alpha-lipoic acid, hyaluronic acid, glycine, gelatin, glucosamine, pickled ume or combinations thereof.

Another embodiment of the invention is a method of improving the appearance, texture, or moisture of skin using a formulation comprising pollen (Royal Jelly), wolfberry extract, Chinese Angelica extract, grape seed extract, Lutein, rose hips, Vitamin C or derivatives thereof, biotin, Vitamin E or derivatives thereof, alpha-lipoic acid, hyaluronic acid, glycine, gelatin, glucosamine, pickled ume or combinations thereof.

In another embodiment, the invention is a method of stimulating the formation of collagen and elastin in the skin using a formulation comprising pollen (Royal Jelly), wolfberry extract, Chinese Angelica extract, grape seed extract, Lutein, rose hips, Vitamin C or derivatives thereof, biotin, Vitamin E or derivatives thereof, alpha-lipoic acid, hyaluronic acid, glycine, gelatin, glucosamine, pickled ume or combinations thereof.

In an alternative embodiment, the invention is a method of decreasing the degradation of collagen and elastin in the skin using a formulation comprising pollen (Royal Jelly), wolfberry extract, Chinese Angelica extract, grape seed extract, Lutein, rose hips, Vitamin C or derivatives thereof, biotin, Vitamin E or derivatives thereof, alpha-lipoic acid, hyaluronic acid, glycine, gelatin, glucosamine, pickled ume or combinations thereof.

In a further embodiment of the invention, the invention is a method of increasing lipid synthesis in skin comprising using formulations of the present invention comprising (Royal Jelly), wolfberry extract, Chinese Angelica extract, grape seed extract, Lutein, rose hips, Vitamin C or derivatives thereof, biotin, Vitamin E or derivatives thereof, alpha-lipoic acid, hyaluronic acid, glycine, gelatin, glucosamine, pickled ume or combinations thereof.

In an alternative embodiment, the invention is a method of decreasing the degradation of lipids in the skin using formulations of the present invention comprising (Royal Jelly), wolfberry extract, Chinese Angelica extract, grape seed extract, Lutein, rose hips, Vitamin C or derivatives thereof, biotin, Vitamin E or derivatives thereof, alpha-lipoic acid, hyaluronic acid, glycine, gelatin, glucosamine, pickled ume or combinations thereof.

BRIEF DESCRIPTION OF THE DRAWINGS

FIG. 1 is a schematic illustrating the structures of collagen and elastin proteins, fibrils, and fibers. FIG. 1(A) illustrates the triple helix structure of collagen, which is formed by three extended protein chains that wrap around one another. The striping on the collagen fibril is caused by the regular repeating arrangement of the collagen molecules within the fibril.

FIG. 1(B) illustrates elastin polypeptide chains cross-linked together with collagen fibrils to form rubber-like, elastic fibers. Each elastin molecule uncoils into a more extended conformation when the fiber is stretched and will recoil spontaneously as soon as the stretching force is relaxed.

FIG. 2 is a graph illustrating the effects of various ingredients of the present invention, either alone or in combination, on collagen synthesis. The data are expressed as % control collagen from untreated control cells. FIG. 2 illustrates that when used alone, Chinese Angelica extract and Cherokee Rose Hips are the most potent inducers of collagen synthesis. FIG. 2 also illustrates that when used in combination, Cherokee Rose Hips ("Rose Hip" or "RH") and Pickled Ume ("Ume") are the most potent inducers of collagen synthesis followed by Cherokee Rose Hips and Wolfberry extract ("Wolf"); Cherokee Rose Hips, Wolfberry extract, and Chinese Angelica extract ("Ang"); and Cherokee Rose Hips and Chinese Angelica extract. In FIG. 2, "GS" indicates grape seed extract.

FIG. 3 is a graph illustrating the effects of various ingredients of the present invention, either alone or in combination, on elastin synthesis. The data are expressed as % control elastin from untreated control cells. FIG. 3 illustrates that when used alone, Chinese Angelica extract ("Ang") and Cherokee Rose Hips ("Rose Hip" or "RH") are the most potent inducers of elastin synthesis. FIG. 3 also illustrates that when used in combination, Cherokee Rose Hips and Pickled Ume ("Ume") are the most potent inducers of elastin synthesis followed by Grape Seed extract ("GS"), Pickled Ume, Wolfberry extract ("Wolf"), and Chinese Angelica extract; and Grape Seed extract, Chinese Angelica extract, and Wolfberry extract.

FIG. 4 is a graph illustrating the effects of various ingredients of the present invention, either alone or in combination, on hyaluronic acid synthesis. The data are expressed as % control hyaluronic acid from untreated control cells. FIG. 4 illustrates that none of the ingredients alone induce significant levels of hyaluronic acid synthesis. However, FIG. 4 also illustrates that when used in combination, Cherokee Rose Hips ("Rose Hip" or "RH"), Wolfberry extract ("Wolf"), and Chinese Angelica extract ("Ang") are the most potent inducers of hyaluronic acid synthesis followed by Cherokee Rose Hips and Chinese Angelica extract; and Grape Seed extract ("GS"), Chinese Angelica extract, and Wolfberry extract.

FIG. 5 is a graph illustrating the effects of various ingredients of the present invention on the enzyme activity of MMP-1 (black), MMP-9 (light gray), and elastase (gray) enzymes. The data are expressed as % control for each enzyme. FIG. 5 illustrates that Royal Jelly was the most potent inhibitor of MMP-1 and Elastase, while Pickled Ume was the most potent inhibitor of MMP-9. Grape seed extract had the least inhibitory effect on any of the three enzymes, followed by Cherokee Rose Hips.

FIG. 6 is a graph illustrating the transport of ingredients of the present invention across Caco-2 monolayers. Data are expressed as % control collagen secreted by co-culture responder cells incubated on the basolateral side of the Caco-2 cells and are compared to untreated control co-cultures.

DETAILED DESCRIPTION

It is to be understood that this invention is not limited to the particular methodology or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

The present invention is based on the surprising discovery that unique combinations of the following ingredients, described more fully in Table 1, improve skin moisture, texture, and appearance: pollen (Royal Jelly), wolfberry extract, Chinese Angelica extract, grape seed extract, rose hips, Pickled ume, Carotenoids, biotin, Vitamin C or derivatives thereof, Vitamin E or derivatives thereof, alpha-lipoic acid, hyaluronic acid, glycine, and glucosamine. More specifically, the formulations of the present invention improve skin moisture, texture, and appearance by increasing the synthesis of skin proteins, such as collagen or elastin, and/or by preventing or slowing the degradation of such proteins. Additionally, the formulations of the present invention have the unique ability to increase the synthesis and/or prevent or slow the degradation of lipids in the skin, which aids in skin moisture.

TABLE 1

Ingredients for Use in Formulations of the Present Invention

| Ingredient Name: | Characteristics: |
|---|---|
| Royal Jelly (pollen) | Royal jelly promotes collagen synthesis in skin fibroblasts in the presence of ascorbic acid-2-O-alpha-glucoside (AA-2G). Koya-Miyata, et al., "Identification of a collagen production-promoting factor from an extract of royal jelly and its possible mechanism." Biosci Biotechnol Biochem. 68(4): 767-73, 2004. Royal jelly also has been shown to induce the fibroblast cell line, NHDF, to produce transforming growth factor-$\beta$1 (TGF-$\beta$1), which is an important factor for collagen production. Oral administration of royal jelly to picryl chloride treated NC/Nga mice inhibits the development of atopic-dermatitis like skin lesions |

TABLE 1-continued

Ingredients for Use in Formulations of the Present Invention

| Ingredient Name: | Characteristics: |
|---|---|
| | in the mice. Taniguchi, et al., "Oral administration of royal jelly inhibits the development of atopic dermatitis-like skin lesions in NC/Nga mice." Int. Immunopharmacol. 3(9): 1313-24, 2003. |
| Wolfberry Extract (*Lycium barbarum*) | *Lycium barbarum*, also commonly referred to as Chinese wolfberry from which wolfberry extract is made, is a deciduous shrub with a long history of medicinal use for a wide range of ailments from skin rashes and eyesight problems to diabetes. Larkcom J. 1991. Oriental Vegetables.<br>Wolfberry extract, which is made from the fruits of *lycium barbarum*, is a rich source of vitamins and minerals, especially in vitamins A, C, and E, flavanoids, and other bio-active compounds. It is also a fairly good source of essential fatty acids. Larkcom J. 1991. Oriental Vegetables. |
| Chinese Angelica Extract (*Angelica sinensis*) | *Angelica sinensis* or Chinese Angelica extract is also known as dong quai or dang gui and is sometimes referred to as the female ginseng. It is an aromatic herb that grows in China, Korea, and Japan.<br>*Angelica sinensis* root contains angelicide, coumarin derivatives including angelol and angelicone, B-sitosterol, butyl phthalide, cadiene, calcium channel-blocking compounds, carvacrox, ferulic acid, flavonoids, fixed oil, furanocoumarins, nicotinic acid, phytosterols, polysaccharides, stigmasterol, vitamins E, A, and B12, as well as essential oils consisting mainly of ligustilide and N-butylidenphthalide. Information available at: http://www.globalherbalsupplies.com/herb_information/dong_quai.htm<br>*Angelica sinensis* promotes melanocyte proliferation, melanin synthesis, and tyrosinase activity. Deng, Y. and L. Yang, "Effect of *Angelica sinensis* on melanocytic proliferation, melanin synthesis and tyrosinase activity in vitro." Di Yi Jun Yi Da Xue Xue Bao. 23(3): 239-41, 2003. |
| Grape Seed Extract | Grape seed extract (GSE) refers to any compound or combination of compounds obtained from grape seed (i.e., lipids, proteins, carbohydrates, polyphenols, catechins, procyanidins, flavonols, oligomeric proanthocyanidins, polymeric proanthocyanidins, gallic acid esters, etc.) and/or to any oils obtained from grape seed, as well as to chemical derivatives thereof.<br>Scientific studies have shown that the antioxidant power of proanthocyanidins found in GSE is 20 times greater than vitamin E and 50 times greater than vitamin C. Extensive research suggests that GSE is beneficial in many areas of health because of its antioxidant effect to bond with collagen, promoting youthful skin, cell health, elasticity, and flexibility. Shi et al., "Polyphenolics in grape seeds - biochemistry and functionality." J. Med. Food. 6(4): 291-9, 2003. Typically, proanthocyanidins are known for their ability to inhibit tyrosinase. For example, see U.S. Pat. No. 6,590,105 and JP 2000-159681 by Hai Tai Confectionary Co. As another example, Yamakoshi et al., report that oral administration of proanthocyanidins in GSE is effective in lightening the UV-induced pigmentation of guinea pig skin. Yamakoshi, et al., "Lightening effect on ultraviolet-induced pigmentation of guinea pig skin by oral administration of a proanthocyanidin-rich extract from grape seeds." Pigment Cell Res. 16(6): 629-38, 2003. Yamakoshi et al., attribute the observed effect of proanthocyanidins to inhibition of melanin synthesis by tyrosinase in melanocytes and the ROS-related proliferation of melanocytes. |
| Cherokee Rose Hips | Cherokee rose hips are derived from the *Rosa laevigata* plant, which is a member of the rose family. The fruit of the Cherokee rose is called a "hip" or "rose hips." Rose hips are a natural source of vitamin C. Information available at: http://www.floridata.com/ref/R/rosalaev.cfm |
| Pickled Ume | Ume is a deciduous tree native to China, which is a member of the Roseaceae family and a close relative of apricot and plum. Pickled ume is typically used to improve the health of the digestive tract. Pickled ume contains organic acids, triterpenoids including oleanolic acid, citric acid, and ascorbic acid, steroids including sitosterol, B-carotene, thiamine, riboflavin, niacin, calcium, phosphorous, iron, sodium, potassium, protein, fats, carbohydrates, and fiber. Information available at: http://www.planetbotanic.ca/fact_sheets/japanese_herbs/ume.htm |
| Carotenoids | Carotenoids are useful oral sun protectants. Indeed, supplementation with high doses of beta-carotene protects against UV-induced erythema. Heinrich, et al., "Supplementation with beta-carotene or a similar amount of mixed carotenoids protects humans from UV-induced erythema." J. Nutr. 133(1): 98-101, 2003. |

TABLE 1-continued

Ingredients for Use in Formulations of the Present Invention

| Ingredient Name: | Characteristics: |
|---|---|
| | Lutein and zeaxanthin are carotenoids found in leafy green vegetables. Oral supplementation of lutein and zeaxanthin diminishes the effects of UVB irradiation. Gonzalez, et al., "Dietary lutein/zeaxanthin decreases ultraviolet B-induced epidermal hyperproliferation and acute inflammation in hairless mice." 2003. J. Invest. Dermatol., 121(2): 399-405.<br>Lycopene, lutein, and zeaxanthin are efficient antioxidants that quench singlet oxygen produced during the photooxidative processes. Thus, lycopene, lutein, and zeaxanthin play a role in preventing light-exposed tissue, including the tissue of the skin and eyes, from light-induced damage. Sies and Stahl report that increasing lycopene intake by daily consumption of tomato paste over a period of ten weeks provides protection against erythema formation following UV-irradiation. Sies, H and W. Stahl, "Non-nutritive bioactive constituents of plants: lycopene, lutein and zeaxanthin." Int. J. Vitam. Nutr. Res. 73(2): 95-100, 2003. |
| Biotin | Biotin is a B-vitamin which assists in metabolism of fats, carbohydrates and protein. Biotin functions as a critical component of several enzymes involved in energy metabolism (such as pyruvate carboxylase).<br>In its physiologically active form biotin is attached at the active site of four important enzymes, known as carboxylases. Chapman-Smith A, Cronan JE, Jr. Molecular biology of biotin attachment to proteins. J Nutr. 1999; 129(2S Suppl): 477S-484S. Each carboxylase catalyzes an essential metabolic reaction:<br>a. Acetyl-CoA carboxylase catalyzes the binding of bicarbonate to acetyl-CoA to form malonyl-CoA. Malonyl-CoA is required for the synthesis of fatty acids.<br>b. Pyruvate carboxylase is a critical enzyme in gluconeogenesis, the formation of glucose from sources other than carbohydrates, for example, amino acids and fats.<br>c. Methylcrotonyl-CoA carboxylase catalyzes an essential step in the metabolism of leucine, an indispensable (essential) amino acid.<br>d. Propionyl-CoA carboxylase catalyzes essential steps in the metabolism of amino acids, cholesterol, and odd chain fatty acids (fatty acids with an odd number of carbon molecules). Zempleni J, Mock DM. Biotin biochemistry and human requirements. 1999; volume 10: pages 128-138. J Nutr. Biochem. 1999; 10: 128-138. |
| Vitamin C | Vitamin C is an antioxidant known both to inhibit melanin formation by reducing o-quinone formation and to reduce oxidized melanin. Vitamin C is a powerful water-soluble antioxidant that has been shown to reduce UVB-induced oxidative damage in mouse keratinocytes in vitro and to protect human keratinocytes from UVA-induced lipid peroxidation. McArdle et al., "UVR-Induced Oxidative Stress in Human Skin In Vivo: Effects of Oral Vitamin C Supplementation." Free Radical Biology & Medicine, Vol. 33, No. 10, pp. 1355-1362, 2002.<br>Ascorbic acid is one of the most common forms of vitamin C. |
| Vitamin E | Vitamin E is a fat-soluble vitamin that exists in eight different forms. Each form has its own biological activity, which is the measure of potency or functional use in the body. Traber MG and Packer L. Vitamin E: Beyond antioxidant function. Am J Clin Nutr 1995. 62: 1501-9.<br>Alpha-tocopherol ($\alpha$-tocopherol) is the name of the most active form of vitamin E in humans. It is also a powerful biological antioxidant. Traber MG. Vitamin E. In: Shils ME, Olson JA, Shike M, Ross AC, ed. Modern Nutrition in Health and Disease. 10th ed. Baltimore: Williams & Wilkins, 1999: 347-62; Farrell P and Roberts R. Vitamin E. In: Shils M, Olson JA, and Shike M, ed. Modern Nutrition in Health and Disease. 8th ed. Philadelphia, PA: Lea and Febiger, 1994: 326-41.<br>Antioxidants such as vitamin E act to protect your cells against the effects of free radicals, such as ROS, which are potentially damaging by-products of energy metabolism. Free radicals can damage cells and may contribute to the aging process as well as to the development of cardiovascular disease and cancer. |
| $\alpha$-lipoic acid | Alpha-lipoic acid neutralizes free radicals in both the fatty and watery regions of cells, in contrast to vitamin C (which is water soluble) and vitamin E (which is fat soluble).<br>The body routinely converts some alpha-lipoic acid to dihydrolipoic acid, which appears to be an even more powerful antioxidant. Both forms of lipoic acid quench peroxynitrite radicals, an especially dangerous type consisting of both oxygen and nitrogen, according to |

TABLE 1-continued

Ingredients for Use in Formulations of the Present Invention

| Ingredient Name: | Characteristics: |
|---|---|
| | a recent paper in FEBS Letters (Whiteman M, et al., FEBS Letters, 1996; 379: 74-6). Alpha-lipoic acid also plays an important role in the synergism of antioxidants. It directly recycles and extends the metabolic lifespans of vitamin C, glutathione, and coenzyme Q10, and it indirectly renews vitamin E. |
| Hyaluronic acid | Hyaluronic acid (HA) is a negatively charged glycosaminoglycan composed of repeated disaccharide of D-glucuronic acid and N-acetylglucosamine. Greco et al., "Hyaluronic Acid Stimulates Human Fibroblast Proliferation Within a Collagen Matrix." J. of Cell. Physiol. 177: 465-473 (1998). Changes in HA concentration within the extracellular matrix modulate a variety of cellular functions such as cell migration, cell adhesion, and cell proliferation. HA interactions with specific cell surface receptors can modulate morphogenesis. Hyaluronic acid occurs naturally in the dermis and is a strong humectant, holding 1000 times its weight in water. Because it is a large molecule, it does not penetrate deeply buts its excellent water-binding ability gives suppleness and plasticity to the epidermis. It forms a film on skin similar to the way it holds water in the intercellular matrix of dermal connective tissues. |
| Glycine | Glycine is essential for the synthesis of nucleic acids, bile acids, and other nonessential amino acids in the body. It is also essential for central nervous system function and for a healthy prostate. Because high concentrations of glycine are found in the skin and connective tissues, it is useful for repairing damaged tissues and promoting healing. Indeed, Glycine retards muscle degeneration by supplying additional creatine, a compound that is present in muscle tissue and it utilized in the construction of DNA and RNA. It also improves glycogen storage, thus freeing up glucose for energy needs. |
| Glucosamine | Glucosamine is made from the combination of a sugar and an amine, which is a derivative of ammonia containing nitrogen (N) and hydrogen (H) atoms. Glucosamine is found largely in cartilage and plays an important role in its health and resiliency. Glucosamine has been studied extensively for treating osteoarthritis (OA), a condition that generally results from wear-and-tear on joints. In OA, deterioration of the cartilage, which cushions the joints, leads to pain, swelling, and loss of movement. Glucosamine is also important for healthy skin. Adequate amounts of it in the blood are necessary for the production of hyaluronic acid, one of the substances essential to heal skin injuries. Therefore, glucosamine plays a major role in the healing of surgical incisions and skin wounds. Because natural production of hyaluronic acid decreases as individuals age, decreases in it may contribute to wrinkling of the skin. It is thought that increasing glucosamine may help the skin stay more resilient. |

Formulations of the Present Invention

The formulations of the present invention are designed to offer a combination of ingredients, rather than just herbal extracts. Specifically, formulations of the present invention comprise a combination of vitamins, amino acids, natural products, and plant extracts. These unique combinations of ingredients target a number of key enzymes involved in skin health, and also modulate cellular activity of skin cells to promote improved skin health. In particular, various ingredients comprising the formulations of the present invention stimulate synthesis and/or inhibit degradation of collagen and/or elastin. For example, Cherokee Rose Hips and Chinese Angelica extract are potent inducers of collagen synthesis, alone or in combination, while other compounds, such as Royal Jelly and Pickled Ume, are effective at inhibiting the activity of MMPs.

As used herein "stimulating collagen (or elastin) synthesis" is used in its broadest sense and refers to the production of collagen or elastin, its incorporation into collagen- or elastin-containing tissue (including, e.g., the synthesis, processing, cross-linking, secretion, and assembly of collagen fibrils or elastin fibers) and the presence of healthy collagen- or elastin-containing tissue. "Stimulating" or "inducing" collagen or elastin synthesis, therefore, refers to the ability of a formulation described herein to positively affect the production of collagen or elastin. Stimulating collagen or elastin synthesis may be brought about by the ability of the formulations described herein to promote steps, such as biochemical steps, leading to the formation of collagen fibrils or elastin fibers.

"Inhibiting degradation of collagen (or elastin)," refers to the ability of a formulation described herein to preserve existing healthy collagen- or elastin-containing tissue, for example, by inhibiting a MMP which inhibits collagen or elastin or by replenishing collagen or elastin to tissue wherein collagen or elastin is broken down by natural processes or disease-associated processes.

As used herein "stimulating lipid synthesis" is used in its broadest sense and refers to the production of lipids in the skin. "Stimulating" or "inducing" lipid synthesis, therefore, refers to the ability of a formulation described herein to positively affect the production of lipids in the skin. Stimulating lipid synthesis may be brought about by the ability of the formulations described herein to promote steps, such as biochemical steps, leading to the formation of lipids in the skin.

The formulations of the present invention are based on combinations of ingredients including plant extracts which are in extract ratios of 20:1, and wherein the extracts are produced using water extraction methods commonly used to prepare herbal extracts in Traditional Chinese Medicine. See Wang et al., "Extraction and Chromatography-Mass Spectromic Analysis of the Active Principles from Selected Chinese Herbs and Other Medicinal Plants." 2003. *Am. J. Chin. Med.* 31(6):927-44.

In one embodiment of the present invention, the formulation comprises the following active ingredients in the following amounts: Royal Jelly (pollen), 30-1500 mg; Wolfberry extract (20:1 extract ratio), 30-500 mg; Chinese Angelica extract (20:1 extract ratio), 30-500 mg; Grape seed extract, 100-150 mg; Lutein, 2-5 mg; Cherokee Rose Hips, 30-500 mg; Vitamin C or derivatives thereof, 40-70 mg; Biotin, 600-900 mg; Vitamin E or derivatives thereof, 3-7 mg; α-lipoic acid, 1-4 mg; hyaluronic acid, 4-60 mg; glycine, 30-200 mg; glucosamine 5-300 mg; and gelatin, 30-500 mg.

In another embodiment, a formulation of the present invention comprises the following active ingredients in the following amounts: Royal jelly (pollen), 30-1500 mg; Wolfberry extract (20:1 extract ratio), 30-500 mg; and Chinese Angelica extract (20:1 extract ratio), 30-500 mg. Alternatively, this formulation can additionally contain one or more of the following active ingredients in the following amounts: Grape seed extract, 100-150 mg; Lutein, 2-5 mg; Cherokee Rose Hips, 30-500 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; Pickled Ume, 10-500 mg; glucosamine 5-300 mg; and gelatin, 30-500 mg.

In a further embodiment, a formulation of the present invention comprises the following active ingredients in the following amounts: Royal jelly (pollen), 30-1500 mg; Wolfberry extract (20:1 extract ratio), 30-500 mg; Chinese Angelica extract (20:1 extract ratio), 30-500 mg; and Cherokee Rose Hips (20:1 extract ratio), 30-500 mg. Alternatively, this formulation can additionally contain one or more of the following active ingredients in the following amounts: Grape seed extract, 100-150 mg; Lutein, 2-5 mg; Cherokee Rose Hips, 30-500 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; Pickled Ume, 10-500 mg; glucosamine 5-300 mg; and gelatin, 30-500 mg.

In an alternative embodiment, a formulation of the present invention comprises the following active ingredients in the following amounts: Chinese Angelica extract (20:1 extract ratio), 30-500 mg and Cherokee Rose Hips (20:1 extract ratio), 30-500 mg. Alternatively, this formulation can additionally contain one or more of the following active ingredients in the following amounts: Royal Jelly (pollen), 30-1500 mg; Wolfberry extract (20:1 extract ratio), 30-500 mg; Grape seed extract, 100-150 mg; Lutein, 2-5 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; Pickled Ume, 10-500 mg; glucosamine 5-300 mg; and gelatin, 30-500 mg.

In another embodiment, a formulation of the present invention comprises the following active ingredients in the following amounts: Cherokee Rose Hips (20:1 extract ratio), 30-500 mg and Pickled Ume (20:1 extract ratio), 10-500 mg. Alternatively, this formulation can additionally contain one or more of the following active ingredients in the following amounts: Royal Jelly (pollen), 30-1500 mg; Wolfberry extract (20:1 extract ratio), 30-500 mg; Chinese Angelica extract (20:1 extract ratio), 30-500 mg; Grape seed extract, 100-150 mg; Lutein, 2-5 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; glucosamine 5-300 mg; and gelatin, 30-500 mg.

In an alternative embodiment, a formulation of the present invention comprises the following active ingredients in the following amounts: Wolfberry extract (20:1 extract ratio), 30-500 mg and Cherokee Rose Hips (20:1 extract ratio), 30-500 mg. Alternatively, this formulation can additionally contain one or more of the following active ingredients in the following amounts: Royal Jelly (pollen), 30-1500 mg; Chinese Angelica extract (20:1 extract ratio), 30-500 mg; Grape seed extract, 100-150 mg; Lutein, 2-5 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; Pickled Ume, 10-500 mg; glucosamine 5-300 mg; and gelatin, 30-500 mg.

In a further embodiment, a formulation of the present invention comprises the following active ingredients in the following amounts: Chinese Angelica extract (20:1 extract ratio), 30-500 mg; Wolfberry extract (20:1 extract ratio), 30-500 mg; and Cherokee Rose Hips (20:1 extract ratio), 30-500 mg. Alternatively, this formulation can additionally contain one or more of the following active ingredients in the following amounts: Royal Jelly (pollen), 30-1500 mg; Grape seed extract, 100-150 mg; Lutein, 2-5 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; Pickled Ume, 10-500 mg; glucosamine 5-300 mg; and gelatin, 30-500 mg.

In another embodiment, a formulation of the present invention comprises the following active ingredients in the following amounts: Grape seed extract, 100-150 mg; Pickled Ume, 10-500 mg; Chinese Angelica extract (20:1 extract ratio), 30-500 mg; and Wolfberry extract (20:1 extract ratio), 30-500 mg. Alternatively, this formulation can additionally contain one or more of the following active ingredients in the following amounts: Royal Jelly (pollen), 30-1500 mg; Lutein, 2-5 mg; Cherokee Rose Hips, 30-500 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; glucosamine 5-300 mg; and gelatin, 30-500 mg.

In one embodiment, a formulation of the present invention comprises the following active ingredients in the following amounts: Grape seed extract, 100-150 mg; Chinese Angelica extract (20:1 extract ratio), 30-500 mg; and Wolfberry extract (20:1 extract ratio), 30-500 mg. Alternatively, this formulation can additionally contain one or more of the following active ingredients in the following amounts: Royal Jelly (pollen), 30-1500 mg; Lutein, 2-5 mg; Cherokee Rose Hips, 30-500 mg; Vitamin C, 40-70 mg; Biotin, 600-900 mg; Vitamin E, 3-7 mg; α-lipoic acid, 1-4 mg; hyaluronic acid, 4-60 mg; glycine, 30-200 mg; Pickled Ume, 10-500 mg; glucosamine 5-100 mg; and gelatin, 30-500 mg.

Methods of Administration

Improved skin appearance, texture, and moisture can be achieved by administering the formulations of the present invention externally, internally, or some combination thereof. Preferably, the formulations of the present invention are administered with an acceptable carrier. For example, the formulation of the present invention could be externally administered with an acceptable carrier in the form of a gel, lotion, cream, tonic, emulsion, etc. As a further example, the formulation of the present invention could be internally administered with an acceptable carrier in the form of a pill, tablet, powder, bar, beverage, etc. Thus, the formulations described herein are useful in a wide variety of finished products, including pharmaceutical products, food products, and beverage compositions. Preferably, the products are useful for providing mammalian skin with an improved texture, appearance, and increased moisture.

In a one embodiment of the invention, the formulations of the present invention are administered orally in the form of a Beauty Shot drink. Oral administration of the formulations of the present invention causes immediate moisturization of the skin and maintains youthful skin.

When the formulations of the present invention are orally administered in the form of a liquid, the liquid may be water-based, milk-based, tea-based, fruit juice-based, or some combination thereof. Solid and liquid formulations for internal administration according to the present invention can further comprise thickeners, including xanthum gum, carbosymethyl-cellulose, carboxyethylcellulose, hydroxyporpolcellulose, methylcellulose, microcrystalline cellulose, starches, dextrins, fermented whey, tofu, maltodextrins, polyols, including sugar alcohols (e.g., sorbitol and mannitol), carbohydrates (e.g. lactose), propylene hlycol alginate, gellan gum, guar, pectin, tragacanth gum, gum acacia, locust bean gum, gum arabic, gelatin, as well as mixtures of these thickeners. These thickeners are typically included in the formulations of the present invention at levels up to about 0.1%, depending on the particular thickener involved and the viscosity effects desired.

The solid and liquid (food and beverage) formulations of the present invention can, and typically will, contain an effective amount of one or more sweeteners, including carbohydrate sweeteners and natural and/or artificial no/low calorie sweeteners. The amount of the sweetener used in the formulations of the present invention will vary, but typically depends on the type of sweetener used and the sweetness intensity desired.

In another embodiment of the invention, the formulations of the present invention are topically administered in the form of a: solution, gel, lotion, cream, ointment, oil-in-water emulsion, water-in-oil emulsion, stick, spray, paste, mousse, tonic, or other cosmetically and topically suitable form.

Preferably, formulations of the present invention that are suitable for topical administration are mixed with an acceptable carrier. An acceptable carrier may act variously as solvent, carrier, diluent or dispersant for the constituents of the composition, and allows for the uniform application of the constituents to the surface of the skin at an appropriate dilution. The acceptable carrier may also facilitate penetration of the composition into the skin.

In one example of a formulation for topical application, the acceptable carrier forms from about 90% to about 99.99% by weight of the total composition. In other examples, the acceptable carrier will form from about 97% to 99% by weight of the total composition. The acceptable carrier may also form from about 91% to about 98% by weight of the total composition; from about 92% to about 97% by weight of the total composition; from about 93% to about 96% by weight of the total composition; or from about 94% to about 95% by weight of the total composition. The acceptable carrier can, in the absence of other cosmetic adjuncts or additives, form the balance of the composition.

The various ingredients used in practicing the present invention may be soluble or insoluble in the acceptable carrier. If all ingredients of a formulation are soluble in the acceptable carrier, then the vehicle acts as solvent. However, if all or some ingredients of a formulation are insoluble in the acceptable carrier, then those ingredients are dispersed in the vehicle by means of, for example, a suspension, emulsion, gel, cream or paste, and the like.

Thus, it will be apparent to the skilled artisan that the range of possible acceptable carriers is very broad. For example, acceptable carriers can be emulsions, lotions, creams, or tonics. Acceptable carriers can comprise water, ethanol, butylene glycol, or other various solvents that aid in penetration of the skin. Some examples of suitable vehicles are described in U.S. Pat. No. 6,184,247 and in U.S. Pat. No. 6,579,516, the entire contents of which are incorporated herein by reference.

Preferably the acceptable carrier used in practicing the present invention comprises water and ethanol. Optionally, the acceptable carrier also contains butylene glycol and/or frescolate MGA. For example, the acceptable carrier can comprise 40-60% water, 45-55% ethanol, and 5-10%% butylene glycol by weight of the composition. In practicing the present invention, preferably this acceptable carrier is mixed with a formulation of the present invention comprising 2% by weight of the total composition. In other embodiments, the acceptable carrier is mixed with a formulation of the present invention comprising 0.99% to 10% by weight of the total composition; 1% to 9% by weight of the total composition; 2% to 8% by weight of the total composition; 3% to 7% by weight of the total composition; or 4% to 6% by weight of the total composition.

In general, however, acceptable carriers according to the present invention may comprise, but are not limited to comprising, any of the following examples: water; castor oil; ethylene glycol monobutyl ether; diethylene glycol monoethyl ether; corn oil; dimethyl sulfoxide; ethylene glycol; isopropanol; soybean oil; glycerin; soluble collagen; zinc oxide; titanium oxide; or Kaolin.

Additionally, acceptable carriers used in the present invention may optionally comprise one or more humectants, including but not limited to: dibutyl phthalate; soluble collagen; sorbitol; or sodium 2-pyrrolidone-5-carboxylate. Other examples of humectants that may be used in practicing the present invention can be found in the CFTA Cosmetic Ingredient Handbook, the relevant portions of which are incorporated herein by reference.

Additionally, acceptable carriers in the present invention may optionally comprise one or more emollients including but not limited to: butane-1,3-diol; cetyl palmitate; dimethylpolysiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride; polyethylene glycol; propane-1,2-diol; triethylene glycol; sesame oil; coconut oil; safflower oil; isoamyl laurate; nonoxynol-9; panthenol; hydrogenated vegetable oil; tocopheryl acetate; tocopheryl linoleate; allantoin; propylene glycol; arachis oil; castor oil; isostearic acid; palmitic acid; isopropyl linoleate; lauryl lactate; myristyl lactate; decyl oleate; or myristyl myristate. Other examples of emollients that may be used in practicing the present invention can be found in the CFTA Cosmetic Ingredient Handbook, the relevant portions of which are incorporated herein by reference.

Additionally, acceptable carriers used in the present invention may optionally comprise one or more penetration enhancers including but not limited to: pyrrolidones, for example 2-pyrrolidone; alcohols, such as ethanol; alkanols, such as decanol; glycols, such as propylene glycol, dipropylene glycol, butylenes glycol; surfactants; or terpenes.

Other acceptable carriers that may be used in practicing the present invention will be apparent to those of skill in the art and are included within the scope of the present invention.

For example, an acceptable carrier can be a lotion that is topically applied. The lotion may comprise cabomer 981, water, glycerin, isopropyl myristate, mineral oil, shea butter, stearic acid, glycol stearate, cetyl alcohol, dimethicone, preservatives, tea, and various ingredients of the formulations of the present invention.

The formulations of the present invention may also contain various known and conventional cosmetic adjuvants so long as they do not detrimentally affect the desired skin improvement and moisturizing effects provided by the formulation. For example, a formulation of the present invention can further include one or more additives or other optional ingredients well known in the art, which can include but are not limited to fillers (e.g., solid, semi-solid, liquid, etc.); carriers; diluents; thickening agents; gelling agents; vitamins, retinoids, and retinols (e.g., vitamin $B_3$, vitamin A, etc.); pigments; fragrances; sunscreens and sunblocks; anti-oxidants and radical scavengers; organic hydroxy acids; exfoliants; skin conditioners; moisturizers; ceramides, pseudoceramides, phospholipids, sphingolipids, cholesterol, glucosamine, pharmaceutically acceptable penetrating agents (e.g., n-decylmethyl sulfoxide, lecithin organogels, tyrosine, lysine, etc.); preservatives; antimicrobial agents; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, such as Aloe Vera, cornflower, witch hazel, elderflower, or cucumber and combinations thereof. Other suitable additives and/or adjuncts are described in U.S. Pat. No. 6,184,247, the entire contents of which are incorporated herein by reference.

The formulation can include additional inactive ingredients, including, but not limited to surfactants, co-solvents, and excipients. Surfactants, such as hydrophilic and hydrophobic surfactants, can be included in the formulations. Particular surfactants can be used based on the on the overall composition of the formulation and the intended delivery of the formulation. Useful surfactants include polyethoxylated (PEG) fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, polysaccharide esters, polyethylene glycol alkyl phenols, polyoxyethylene-polyoxypropylene block copolymers, sorbitan fatty acid esters, lower alcohol fatty acid esters, ionic surfactants, and mixtures thereof.

The formulations can also include co-solvents such as alcohols and polyols, polyethylene glycols ethers, amides, esters, other suitable co-solvents, and mixtures thereof. The formulations can also include excipients or additives such as sweeteners, flavorants, colorants, antioxidants, preservatives, chelating agents, viscomodulators, tonicifiers, odorants, opacifiers, suspending agents, binders, and mixtures thereof.

Generally, the formulations of the present invention are topically or orally administered at least on a daily basis for a period of time sufficient to bring about the desired level of improvement in skin appearance, texture, and moisture. Topical application or oral administration of the formulations of the invention may continue for any suitable period of time. More specifically, within a few hours to within a few days of the initial application or ingestion, a user may notice the skin has an improved appearance, texture, and moisture. It should be appreciated that the frequency with which the formulations of the present invention should be applied or ingested will vary depending on the desired level improved appearance, texture, and moisture. In particular, the degree of cosmetic enhancement will vary directly with the total amount of composition used.

Useful dosage forms can be prepared by methods and techniques that will be well understood by those of skill in the art and may include the use of additional ingredients in producing tablets, capsules, or liquid dosage forms.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

EXAMPLES

Example 1

Stimulation of Pro-Collagen Synthesis Using Ingredients of the Formulation of the Present Invention Hs27, a human fibroblast cell culture and HEK, a human keratinocyte cell culture, were established in 24 well plates. The cells were exposed to various ingredients used in formulations of the present invention at concentrations of 10 mg/ml. The co-cultures were then incubated overnight. The following day, supernatants were collected. The supernatants were analyzed for the presence of pro-collagen, a soluble precursor of collagen formed by fibroblasts in the process of collagen synthesis. Pro-collagen synthesis was assayed using commercially available ELISA kits. See e.g., Hasan A, Murata H, Falabella A, Ochoa S, Zhou L, Badiavas E, Falanga V. "Dermal fibroblasts from venous ulcers are unresponsive to the action of transforming growth factor-beta 1." *J Dermatol Sci.* 1997. 16(1):59-66.

As illustrated by FIG. 2, when used alone, pickled ume, rose hips, and Chinese Angelic extract were the most potent stimulators of pro-collagen synthesis in fibroblast/keratinocyte co-cultures. Additionally, FIG. 2 illustrates that combinations of rose hips with pickled ume, wolfberry extract, and Chinese Angelica extract induced higher levels of collagen synthesis than any of the compounds alone.

Example 2

Stimulation of Elastin Synthesis Using Ingredients of the Formulation of the Present Invention Hs27, a human fibroblast cell culture and HEK, a human keratinocyte cell culture, were established in 24 well plates. The cells were exposed to various ingredients of the formulations of the present invention at concentrations of 10 mg/ml. The co-cultures were then incubated overnight. The following day supernatants were collected. The supernatants were analyzed for the presence of elastin using the Fastin Elastin® kit from Biocolor. Liao J., Vessely I. 2004. "Relationship between collagen fibrils, glycosaminoglycans, and stress relaxation in mitral valve chordae tendineae." *Ann. Biomed. Eng.* 32(7):977-983.

As demonstrated in FIG. 3, Chinese Angelica extract was the most potent inducer, either alone or in combination, of elastin synthesis.

Example 3

Stimulation of Hyaluronic Acid Synthesis Using Ingredients of the Formulation of the Present Invention Hs27, a human fibroblast cell culture and HEK, a human keratinocyte cell culture, were established in 24 well plates. The cells were exposed to various ingredients of the formulations of the present invention at concentrations of 10 mg/ml. The co-cultures were then incubated overnight. The following day supernatants were collected. The supernatants were analyzed for the presence of hyaluronic acid. Hyaluronic acid synthesis was assayed using commercially available ELISA kits. Lindqvist U., Chichibu K., Delpech B., Goldberg R L, Knudson W., Poole A R, Laurent T C. 1992. "Seven different assays of hyaluronan compared for clinical utility." *Clin. Chem.* 38(1):127-32.

As illustrated in FIG. 4, none of the ingredients alone induce significant levels of hyaluronic acid synthesis, but combinations of rose hips and wolfberry, or rose hips, wolfberry, and Chinese Angelica extract induced higher levels of hyaluronic acid than untreated control cells.

Example 4

Inhibition of MMP-1, MMP-9, and Elastase by Ingredients of the Formulation of the Present Invention Commercially available kits were used for testing the effect of various ingredients used in the formulations of the present invention on the activity of the MMP-1, MMP-9, and elastase. Gould L J, Yager D R, McGeehan G M, Diegelmann R F. 1999. "Method to analyze collagenase and gelatinase activity by fibroblasts in culture." *In Vitro Cell. Dev. Biol. Anim.* 35(2):75-79. For MMP-1, a kit from Amersham® was used according to the manufacturer's specifications. For MMP-9 and Elastase, kits from Molecular Probes® were used. The samples were prepared in stock solvent at stock concentrations of 100 mg/ml. The samples were diluted to 100 μg/ml using PBS.

FIG. 5 illustrates the results of these analyses. Royal Jelly was the most potent inhibitor of MMP-1 and Elastase, while Pickled Ume was the most potent inhibitor of MMP-9. Grape seed extract had the least inhibitory effect on any of the three enzymes, followed by Cherokee Rose Hips.

Example 5

Stimulation of Lipid Synthesis Using Ingredients of the Formulation of the Present Invention Human HEK001 cells were plated at $2 \times 10^4$/well in 96 well plates and were incubated overnight. The following day, the cells were exposed to: glycine, Cherokee rose hips, grape seed extract, Wolfberry extract, Pickled Ume, Ascorbic acid, Chinese Angelica extract, royal jelly, and α-tocopherol, which were diluted into cell culture media at concentrations of 0.005%, 0.05%, and 0.5%.

The cells were then again incubated overnight. The following day, the cells were fixed in 1% formaldehyde. Cellular lipids were then stained with Oil Red O® stain. See Ramirez J L, Castro-Munnozledo F, Kuri-Harusch W. 1992. "Quantitation of adipose conversion and triglycerides by staining intracytoplasmic lipids with Oil Red O." *Histochemistry.* 97:493-497. Following staining, the lipid bound stain was extracted with isopropanol. The OD of the extracted stain was read at 515 nm.

Grape Seed extract was the most potent inducer of lipid synthesis, but Cherokee rose hips and α-tocopherol also demonstrated the ability to induce lipid synthesis.

Example 6

Effect of Various Ingredients on Formation of collagen, Elastin, MMP-1, MMP-9, and Lipids Table 2 summarizes the results of the bioassays discussed in Examples 1-5 and illustrates the effects of glycine, Cherokee rose hips, grape seed extract, wolfberry extract, pickled ume, ascorbic acid, Chinese Angelica extract, royal jelly, and α-tocopherol on formation of collagen, elastin, MMP-1, MMP-9, and lipids. In Table 2, a "+" sign indicates an increase in synthesis, with multiple "+" signs indicating a higher increase in synthesis while a "−" sign indicates decrease in synthesis with multiple "−"signs indicating a higher decrease in synthesis. "NT" indicates that a particular compound's effect on collagen, elastin, MMP-1, MMP-9, elastase, or lipid formation was not tested.

TABLE 2

Effects of Ingredients used in Formulations of the Invention

| Name | Collagen | Elastin | MMP-1 | MMP-9 | Elastase | Lipids |
|---|---|---|---|---|---|---|
| Glycine | + | − | NT | NT | NT | − |
| Cherokee rose hips | ++ | − | +++ | ++ | + | + |
| Grape seed extract | ++ | − | ++++ | ++++ | +++ | +++ |
| Wolfberry extract | +++ | + | − | + | + | − |
| Pickled Ume | +++ | + | − | − | − | − |
| Ascorbic acid | ++++ | + | NT | NT | NT | − |
| Chinese Angelica extract | ++ | ++ | + | + | − | − |
| Royal Jelly | − | − | − | − | −− | − |
| α-tocopherol | − | − | − | − | − | + |

Example 7

Transportation of Ingredients of the Formulation Across Caco-2 Monolayers

High oral absorption levels are critical for the success of any orally administered formulation of the invention. Differentiated Caco-2 cell monolayers exhibit morphological and physiological properties of the human small intestine, e.g., barrier function, microvilli, brush-border enzymes, active transport systems, and efflux systems. Therefore, Caco-2 cells provide a reliable in vitro model to predict in vivo intestinal absorption.

Caco-2 cells are grown on transwell polycarbonate inserts for 21 days. Growth and differentiation is monitored by the measurement of the transepithelial electrical resistance during culture. The test compound is added in triplicate in the donor compartment. Samples are collected from the receiver compartment at specified time points. To assess the influence of P-glycoprotein on the transport process of a compound, the apical-to-basolateral vs. basolateral-to-apical transport is compared. For quality control and for classification of test compounds reference compounds with a high and low transepithelial flux are included in each assay. Reference compounds may be chosen from a compound list provided by Pharmacelsus®. After each assay, the integrity of each cell monolayer is checked by the determination of the permeability coefficient value ($P_{app}$) of Lucifer yellow.

Compound concentrations are measured in the receiver and donor compartments by UV-spectroscopy or by LC-MS/MS. These concentration values are used for the calculation of the apparent permeability and the recovery of a compound.

FIG. 6 illustrates the transport of Cherokee rose hips, wolfberry extract, pickled ume, grape seed extract, Chinese angelica extract, and royal jelly across Caco-2 monolayers. Data are expressed as % control collagen secreted by co-culture responder cells incubated on the basolateral side of the Caco-2 cells and are compared to untreated control co-cultures.

The invention claimed is:

1. A method of increasing lipid synthesis in a skin cell of a subject comprising administering a formulation comprising grape seed extract, wolfberry extract, rosehip, and an acceptable carrier to the subject, wherein the grape seed extract, wolfberry extract, and rosehip increases lipid synthesis in the skin cell.

2. The method of claim 1 wherein the formulation is orally administered in the form of a liquid.

3. The method of claim 2 wherein the liquid is water-based, milk-based, tea-based, fruit-juice based, or some combination thereof.

4. The method of claim 3, wherein the liquid further comprises thickeners, sweeteners, or some combination thereof.

5. The method of claim 1, wherein the formulation is topically administered in the form of a gel, lotion, cream, ointment, emulsion, paste, or mousse.

6. A method of increasing lipid synthesis in a skin cell of a subject comprising administering the formulation of claim 1 to the subject, wherein the formulation further comprises lutein, ascorbic acid, biotin, and glycine, and further wherein the grape seed extract, wolfberry extract, and rosehip increases lipid synthesis in the skin cell.

7. The method of claim 6 wherein the formulation is orally administered in the form of a liquid.

8. The method of claim 7, wherein the liquid is water-based, milk-based, tea-based, fruit-juice based, or some combination thereof.

9. The method of claim 8, wherein the liquid further comprises thickeners, sweeteners, or some combination thereof.

10. The method of claim 6, wherein the formulation is topically administered in the form of a gel, lotion, cream, ointment, emulsion, paste, or mousse.

11. The method of claim 1, wherein the formulation further comprises a-tocopherol.

12. The method of claim 1, wherein the formulation further comprises Chinese angelica extract.

13. The method of claim 1, wherein the formulation further comprises pickled ume extract.

14. The method of claim 1, wherein the formulation comprises 100-150 mg grape seed extract, 30-500 mg wolfberry extract, and 30-500 mg rosehips.

15. The method of claim 14, wherein the formulation further comprises hyaluronic acid in an amount ranging from 4-60 mg.

16. The method of claim 14, wherein the formulation further comprises α-tocohpherol in an amount ranging from 3-7 mg.

17. The method of claim 14, wherein the formulation further comprises Chinese angelica extract in an amount ranging from 30-500 mg.

18. The method of claim 14, wherein the formulation further comprises pickled ume extract in an amount ranging from 30-500 mg.

19. A method of increasing lipid synthesis in a skin cell of a subject comprising administering the formulation of claim 14 to the subject, wherein the formulation further comprises lutein in an amount ranging from 2-5 mg, ascorbic acid in an amount ranging from 40-70 mg, biotin in an amount ranging from 600-900 mg, and glycine in an amount ranging from 30-200 mg.

* * * * *

UNITED STATES PATENT AND TRADEMARK OFFICE
CERTIFICATE OF CORRECTION

PATENT NO. : 7,348,034 B2 Page 1 of 1
APPLICATION NO. : 11/075006
DATED : March 25, 2008
INVENTOR(S) : Mary A. Murray et al.

It is certified that error appears in the above-identified patent and that said Letters Patent is hereby corrected as shown below:

In the Claims

In column 19, in claim 1, line 5, after "and rosehip" delete "increases" and substitute --increase-- in its place.

In columns 19-20, in claim 6, line 6, before "lipid synthesis" delete "increases" and substitute --increase-- in its place.

In column 20, in claim 11, line 2, after "further comprises" delete "a-tocopherol" and substitute --α-tocopherol-- in its place.

In column 20, in claim 16, line 2, after "further comprises" delete "α-tocohpherol" and substitute --α-tocopherol-- in its place.

In column 20, in claim 18, line 3, after "from" delete "30-500" and substitute --10-500-- in its place.

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,348,034 B2 | Page 1 of 1 |
| APPLICATION NO. | : 11/075006 | |
| DATED | : March 25, 2008 | |
| INVENTOR(S) | : Mary A. Murray et al. | |

It is certified that error appears in the above-identified patent and that said Letters Patent is hereby corrected as shown below:

In the Claims

In column 19, in claim 1, line 30, after "and rosehip" delete "increases" and substitute --increase-- in its place.

In column 20, in claim 6, line 3, before "lipid synthesis" delete "increases" and substitute --increase-- in its place.

In column 20, in claim 11, line 16, after "further comprises" delete "a-tocopherol" and substitute --α-tocopherol-- in its place.

In column 20, in claim 16, line 29, after "further comprises" delete "α-tocohpherol" and substitute --α-tocopherol-- in its place.

In column 20, in claim 18, line 36, after "from" delete "30-500" and substitute --10-500-- in its place.

This certificate supersedes the Certificate of Correction issued November 18, 2008.

Signed and Sealed this

Ninth Day of December, 2008

JON W. DUDAS
*Director of the United States Patent and Trademark Office*